(12) United States Patent
Inoue

(10) Patent No.: US 9,740,820 B2
(45) Date of Patent: Aug. 22, 2017

(54) CONTROL APPARATUS AND AUTHENTICATION METHOD

(71) Applicant: OMRON HEALTHCARE CO., LTD., Muko-shi, Kyoto (JP)

(72) Inventor: Tomonori Inoue, Kyoto (JP)

(73) Assignee: FUKUDA DENSHI CO., LTD., Tokyo (JP)

( * ) Notice: Subject to any disclaimer, the term of this patent is extended or adjusted under 35 U.S.C. 154(b) by 241 days.

(21) Appl. No.: 13/953,192

(22) Filed: Jul. 29, 2013

(65) Prior Publication Data
US 2013/0311104 A1 Nov. 21, 2013

Related U.S. Application Data

(63) Continuation of application No. PCT/JP2012/050179, filed on Jan. 6, 2012.

(30) Foreign Application Priority Data

Mar. 23, 2011 (JP) ................................. 2011-064396

(51) Int. Cl.
*G06F 19/00* (2011.01)
*A61B 5/117* (2016.01)

(52) U.S. Cl.
CPC ............ *G06F 19/32* (2013.01); *G06F 19/322* (2013.01); *G06F 19/3418* (2013.01); *A61B 5/117* (2013.01)

(58) Field of Classification Search
None
See application file for complete search history.

(56) References Cited

U.S. PATENT DOCUMENTS 7,328,130 B2 * 2/2008 Wiles ................. G01M 13/025
702/183
2003/0158707 A1 * 8/2003 Doi .............................. 702/187
(Continued)

FOREIGN PATENT DOCUMENTS

CN 1946338 A 4/2007
JP A-2007-144141 6/2007
(Continued)

OTHER PUBLICATIONS

Office Action issued in Chinese Application No. 201280014123.X dated Oct. 8, 2014 (with translation).
(Continued)

*Primary Examiner* — Elaine Gort
*Assistant Examiner* — Evangeline Barr
(74) *Attorney, Agent, or Firm* — Oliff PLC

(57) ABSTRACT

A blood pressure meter, a thermometer, and a pulse oximeter are connected to the control apparatus, and the control apparatus includes an input unit configured to wirelessly input information identifying a measurement time and unique information along with the measurement value from the measurement devices, a processing unit configured to store the inputted measurement value and unique information in a memory, and an authentication unit configured to authenticate the measurement device that inputted the measurement value as being the same as a measurement device that inputted a stored measurement value by comparing the unique information with unique information stored along with a measurement value measured prior to the inputted measurement value. Here, the processing unit is configured to store the inputted measurement value in the case where the authentication succeeds.

6 Claims, 10 Drawing Sheets

(56) References Cited

U.S. PATENT DOCUMENTS

| | | | |
|---|---|---|---|
| 2004/0262046 A1 | 12/2004 | Simond et al. | |
| 2007/0213938 A1* | 9/2007 | Kai | 702/19 |
| 2009/0143687 A1 | 6/2009 | Giersiepen et al. | |
| 2011/0167133 A1* | 7/2011 | Jain | 709/219 |
| 2012/0030229 A1* | 2/2012 | Ji et al. | 707/769 |

FOREIGN PATENT DOCUMENTS

| | | |
|---|---|---|
| JP | A-2007-310759 | 11/2007 |
| JP | A-2008-539481 | 11/2008 |
| JP | A-2010-154881 | 7/2010 |
| WO | WO 01/93143 A1 | 12/2001 |
| WO | WO 2005/104933 A1 | 11/2005 |

OTHER PUBLICATIONS

International Search Report issued in International Patent Application No. PCT/JP2012/050179 dated Mar. 6, 2012.

Mar. 30, 2016 Office Action issued in Russian Patent Application No. 2013147170/14.

\* cited by examiner

FIG. 10

```
PATIENT ID      0000012
PATIENT NAME   ○○ ○○
```

| BLOOD PRESSURE<br>SYSTOLIC  NO MEASUREMENT<br>DIASTOLIC NO MEASUREMENT | PULSE<br>    NO MEASUREMENT |
|---|---|
| BODY TEMPERATURE<br>    NO MEASUREMENT | SpO2<br>    NO MEASUREMENT |

FIG. 11

```
PATIENT ID      0000012
PATIENT NAME   ○○ ○○
```

| BLOOD PRESSURE<br>SYSTOLIC  128mmHg<br>DIASTOLIC  78mmHg | PULSE<br>    68bpm |
|---|---|
| BODY TEMPERATURE<br>    36.5°C | SpO2<br>    99% |

… # CONTROL APPARATUS AND AUTHENTICATION METHOD

TECHNICAL FIELD

The present invention relates to control apparatuses and authentication methods, and particularly relates to a control apparatus for controlling a measurement device belonging to a biological information monitor and an authentication method used in such a control apparatus.

BACKGROUND ART

As electronic medical records become widespread, measurement devices for measuring inpatients' biological values are increasingly being connected to networks. A procedural system in which an inpatient measures a biological value such as body temperature him/herself and a nurse then checks that value and adds the value to an electronic medical record is also becoming widespread.

In such a system, it is essential for the biological values to be associated with the patient to which the values belong in order to reduce the risk of mixing up patients.

A biological information monitor is generally a single unit in which respective measurement devices for measuring various types of biological information are integrated into a single housing, and the respective measurement devices are separated from the stated single housing and affixed to respective measurement areas of a patient. Measurement values from the respective measurement devices are associated with the same patient and written into the patient's electronic medical record, and are then handled as the biological information of that patient.

To reduce the risk of data tampering, electronic medical records are sometimes configured so that the recording of data cannot be changed once that data is registered in a server. Accordingly, before biological values are registered in an electronic medical record, it is necessary to confirm the validity of the association.

With respect to this point, employing a technique such as that disclosed in, for example, JP 2007-310759A ("Patent Literature 1" hereinafter), in which an IC tag affixed to a patient is read by a measurement device, makes it possible to associate measurement values with a patient.

CITATION LIST

Patent Literature
Patent Literature 1 JP 2007-310759A

SUMMARY OF INVENTION

Technical Problem

However, the technique disclosed in Patent Literature 1 is problematic in that it is necessary to perform operations for using a measurement device to read the IC tag affixed to the patient each time a measurement is taken, which complicates the operations, and in that it is necessary to provide a reading device in the measurement device, which increases the size of the measurement device and leads to an increase in costs.

There is a further problem in that it is necessary to perform operations for registering identification information stored in the IC tag as identification information of the corresponding patient in advance, which complicates the operations.

Thus what is needed is a technique for associating biological values obtained through measurements made by a measurement device with a patient without requiring special operations such as pre-registration or the like.

Having been achieved in light of such problems, it is an object of the present disclosure to provide a control apparatus capable of associating biological values obtained through measurements made by a measurement device with a patient, without requiring special operations such as pre-registration or the like, and to provide an authentication method used in such a control apparatus.

Solution to Problem

According to one aspect of the invention, a control apparatus for performing a process of storing a measurement value from a measurement device is provided. The control apparatus includes an input unit configured to input information identifying a measurement time and unique information of the measurement device along with the measurement value from the measurement device, a storage unit configured to store the information identifying a measurement time and the unique information along with the measurement value, and a computation unit configured to execute a process for storing the measurement value in the storage unit. The computation unit has an authentication unit configured to compare the unique information inputted along with the measurement value through the input unit with unique information stored in the storage unit along with a measurement value taken prior to the inputted measurement value and authenticate the measurement device that inputted the measurement value as being the same as a measurement device that inputted the measurement value stored in the storage unit, a processing unit configured to store the measurement value in the storage unit in accordance with a result of the authentication performed by the authentication unit, and an output unit configured to output the result of the authentication. The processing unit is configured to store the measurement value in the storage unit along with the unique information in the case where the authentication unit has successfully authenticated the measurement device.

Preferably, the control apparatus is included in a first measurement device for measuring biological information. Here, the storage unit is configured to store a measurement value obtained by the first measurement device and a measurement value obtained by a second measurement device for measuring biological information that is different from the first measurement device. Furthermore, the processing unit is configured to associate a first measurement value obtained by the first measurement device with a second measurement value obtained by the second measurement device and store the associated first measurement value and second measurement value in the storage unit along with the unique information in the case where the second measurement device has been successfully authenticated.

Preferably, the output unit is configured to output information indicating that the authentication unit has failed to authenticate the second measurement device in the case where the authentication unit has failed to authenticate the second measurement device.

Preferably, the processing unit is configured to store the unique information of the second measurement device in the storage unit along with the measurement value obtained by the second measurement device in the case where the authentication of the second measurement device has failed. Here, the authentication unit is configured to use the unique information of the second measurement device whose authentication has failed in the next authentication after the failed authentication.

Preferably, the input unit is configured to accept an input of information identifying a measurement subject corresponding to the measurement value obtained by the first measurement device. Here, the processing unit is configured to associate the first measurement value obtained by the first measurement device with the second measurement value obtained by the second measurement device and the information identifying the measurement subject, and store the associated first measurement value, second measurement value, and information identifying the measurement subject in the storage unit along with the unique information, in the case where the second measurement device has been successfully authenticated.

Preferably, the input unit is configured to accept the input of information identifying a first measurement time that is a measurement time of the first measurement value and a second measurement time that is a measurement time of the second measurement value. Here, the processing unit is configured to associate the first measurement value with the second measurement value and store the associated first measurement value and second measurement value along with the unique information in the storage unit in the case where the second measurement device has been authenticated successfully and the first measurement time and the second measurement time are within a predefined interval.

Preferably, the processing unit is configured to associate the first measurement value with the second measurement value and store the associated first measurement value and second measurement value along with the unique information in the storage unit on a measurement time-by-measurement time basis.

According to another aspect of the invention, an authentication method for authenticating a measurement device for measuring biological information as a measurement device that is associated with a control apparatus is provided. The control apparatus is connected to the storage device. The authentication method includes a step of the control apparatus accepting the input of information identifying a measurement time and unique information of the measurement device along with a measurement value from the measurement device, a step of comparing the inputted unique information with unique information stored in the storage device along with a measurement value taken prior to the inputted measurement value, and a step of storing the inputted measurement value in the storage device along with the unique information in the case where it has been confirmed in the step of comparing that the inputted unique information matches the unique information stored in the storage device and the measurement device that inputted the measurement value has thus been determined to be the same measurement device as the measurement device that inputted the measurement value stored in the storage device.

Advantageous Effects of Invention

According to an aspect of the invention, a biological value obtained through measurement performed by a measurement device can be associated with a patient through a simple process and without requiring a special operation such as registering information in advance.

These and other objects, features, aspects, and advantages of the invention will be made clear through the following detailed descriptions when taken along with the appended drawings.

BRIEF DESCRIPTION OF DRAWINGS

FIG. 10 is a diagram illustrating an example of a screen generated by the control apparatus.

FIG. 11 is a diagram illustrating an example of a screen generated by the control apparatus.

DESCRIPTION OF EMBODIMENTS

Figure 1:
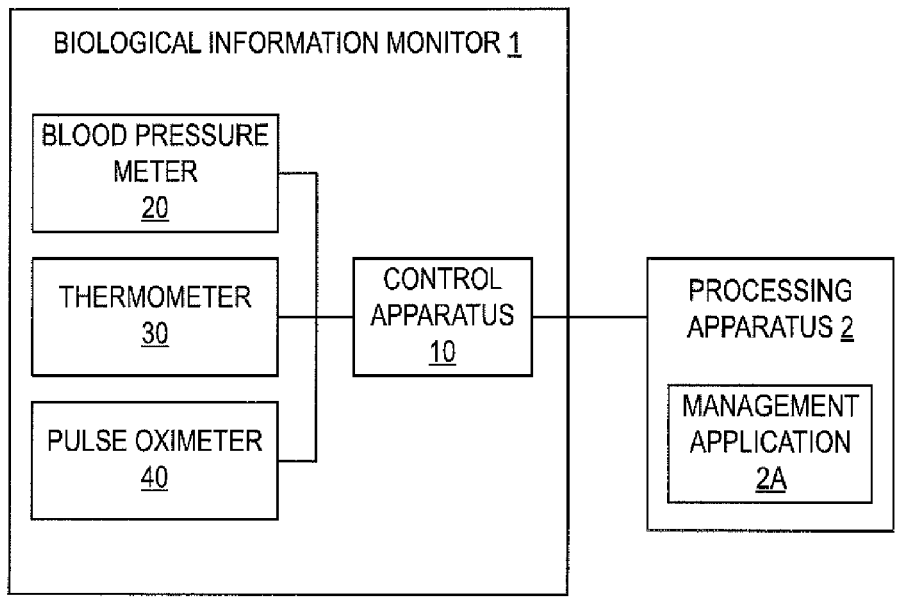
FIG. 1 is a diagram illustrating a specific example of the configuration of a biological information monitor according to an embodiment.

Hereinafter, an embodiment of the present invention will be described with reference to the drawings. In the following descriptions, identical reference numerals are added to identical components or constituent elements. The names and functions thereof are also the same. Accordingly, detailed descriptions thereof will not be repeated.

System Configuration

FIG. 1 is a diagram illustrating a specific example of the configuration of a system for managing biological information according to the present embodiment. In the following descriptions, the system illustrated in FIG. 1 will also be referred to as a "biological information monitor".

As shown in FIG. 1, a biological information monitor 1 according to the present embodiment includes a blood pressure meter 20, a thermometer 30, and a pulse oximeter 40 that serve as measurement devices for measuring biological information, and also includes a control apparatus 10 that is electrically connected to the measurement devices. The biological information monitor 1 includes at least two measurement devices. The measurement devices that are included are not limited to these measurement devices, and other measurement devices may be included instead of or in addition to these measurement devices.

The control apparatus 10 is communicably connected to the blood pressure meter 20, the thermometer 30, and the pulse oximeter 40 that serve as the measurement devices. Although the communication is not limited to any specific type of communication, it is preferable to employ wireless communication. Examples of such wireless communication include RFID (Radio Frequency Identification), which employs radio waves; Bluetooth®, which employs infrared light; wireless communication over a wireless LAN (Local Area Network); wireless communication based on standards such as Zigbee®, ANT, or the like; and so on. Communication via the human body (so-called "human body communication") may also be employed.

The control apparatus 10 included in the biological information monitor 1 is further electrically connected to a processing apparatus 2. The processing apparatus 2 is an apparatus configured of a generic personal computer or the like, and a management application 2A for managing measurement values obtained from a measurement subject, such as an electronic medical record or the like, is installed in the processing apparatus 2.

The communication between the control apparatus 10 and the processing apparatus 2 included in the biological information monitor 1 is not limited to any specific type of communication, and may be communication over a dedicated line, communication via a network such as a LAN, the Internet, or the like, or the same type of wireless communication that is employed between the control apparatus 10 and the measurement devices.

Although FIG. 1 illustrates an example in which a single biological information monitor 1 is connected to a single processing apparatus 2, a plurality of biological information monitors 1 may be connected to a single processing apparatus 2.

The control apparatus 10 is configured of an apparatus such as a generic personal computer. The control apparatus 10 receives measurement values from the blood pressure meter 20, the thermometer 30, and the pulse oximeter 40 respectively, via wireless communication, and carries out processing using those values. The post-processing information is then transmitted to the processing apparatus 2. A display unit 13 (see FIG. 5) is also provided, and the post-processing information is displayed therein.

Apparatus Configuration

Figure 2:
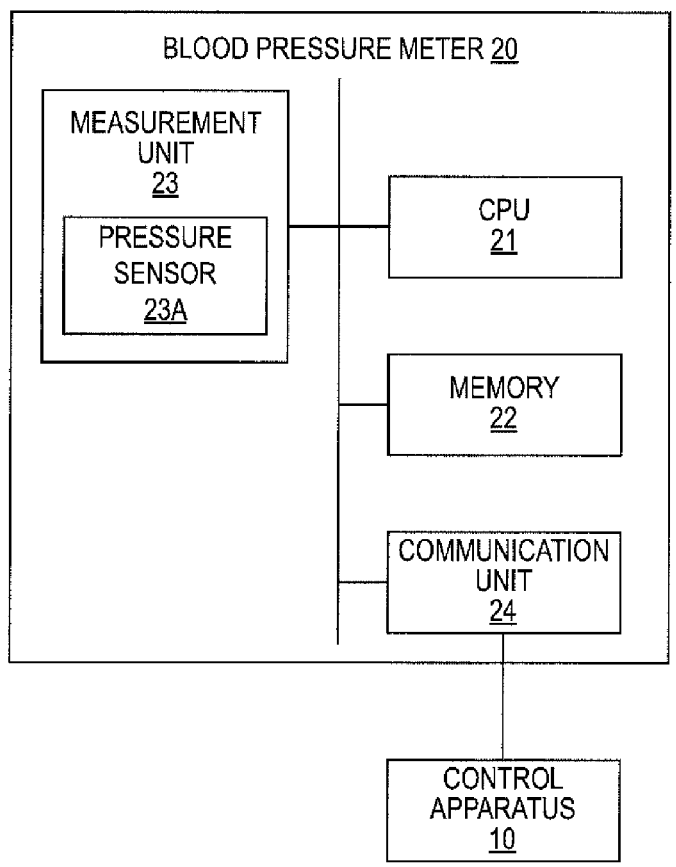
FIG. 2 is a block diagram illustrating a specific example of the device configuration of a blood pressure meter belonging to the biological information monitor.

FIG. 2 is a block diagram illustrating a specific example of the device configuration of the blood pressure meter 20.

The blood pressure meter 20 has essentially the same configuration as a typical blood pressure meter. Specifically, as shown in FIG. 2, the blood pressure meter 20 includes: a CPU (Central Processing Unit) 21 for controlling the blood pressure meter 20 as a whole; a memory 22 for storing programs executed by the CPU 21, measurement values, a measurement device ID serving as identification information of the blood pressure meter 20, and so on; a measurement unit 23 for executing a measurement operation; and a communication unit 24 for carrying out the aforementioned wireless communication with the control apparatus 10.

The blood pressure meter 20 is connected to a measurement band (not shown) that contains an air bladder (a cuff). The measurement band is wrapped around a measurement area such as the upper arm, the wrist, or the like of the measurement subject, and pressure changes in an artery below the skin at the measurement area are transmitted through the air bladder. The measurement unit 23 includes a pressure sensor 23A for measuring an internal pressure of the air bladder and an internal pressure adjustment mechanism (not shown) for the air bladder, and a blood pressure of the measurement subject is measured based on changes in the internal pressure of the air bladder obtained by the pressure sensor 23A as the internal pressure of the air bladder is adjusted according to a specified pattern.

Figure 3:
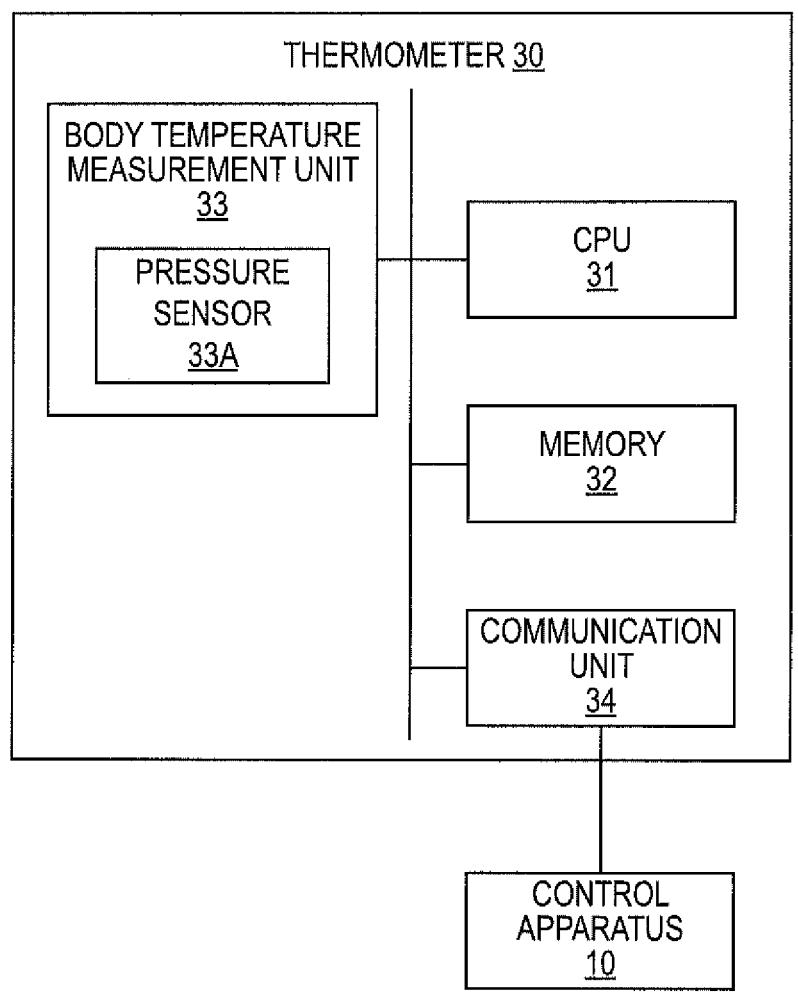
FIG. 3 is a block diagram illustrating a specific example of the device configuration of a thermometer belonging to the biological information monitor.

FIG. 3 is a block diagram illustrating a specific example of the device configuration of the thermometer 30.

The thermometer 30 has essentially the same configuration as a typical electronic thermometer. Specifically, as shown in FIG. 3, the thermometer 30 includes: a CPU 31 for controlling the thermometer 30 as a whole; a memory 32 for storing programs executed by the CPU 31, measurement values, and a measurement device ID serving as identification information of the thermometer 30; a body temperature measurement unit 33 for measuring a body temperature; and a communication unit 34 for carrying out the aforementioned wireless communication with the control apparatus 10.

The body temperature measurement unit 33 includes a temperature sensor 33A, such as a thermistor, provided in a position to which heat can be transmitted from the surface of a housing. A long, thin measurement portion of the thermometer 30, called a probe portion, makes contact with the measurement subject by being inserted into a measurement area such as the underarm, under the tongue, or the rectum, and heat is transmitted from the surface of the housing thereof; this heat causes a resistance value of the temperature sensor 33A to change. The body temperature measurement unit 33 measures the body temperature of the measurement subject based on the resistance value of the temperature sensor 33A.

Figure 4:
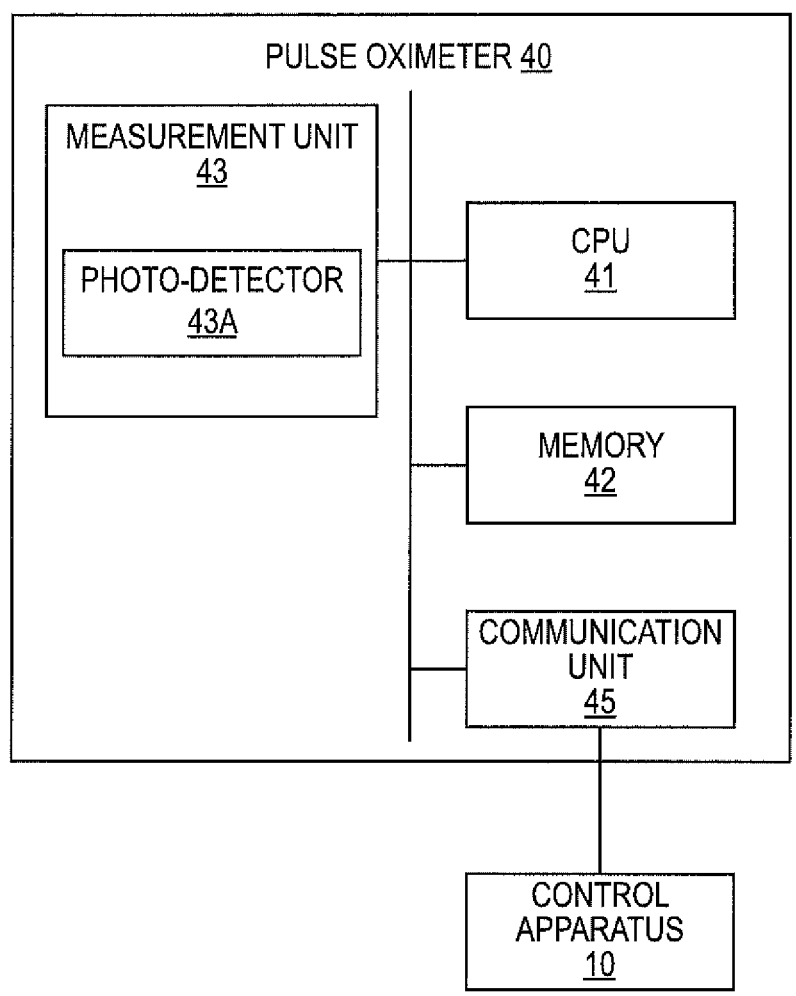
FIG. 4 is a block diagram illustrating a specific example of the device configuration of a pulse oximeter belonging to the biological information monitor.

FIG. 4 is a block diagram illustrating a specific example of the device configuration of the pulse oximeter 40.

The pulse oximeter 40 has essentially the same configuration as a typical pulse oximeter. Specifically, as shown in FIG. 4, the pulse oximeter 40 includes: a CPU 41 for controlling the pulse oximeter 40 as a whole; a memory 42 for storing programs executed by the CPU 41, measurement values, a measurement device ID serving as identification information of the pulse oximeter 40, and so on; a measurement unit 43 for executing a measurement operation; and a communication unit 45 for carrying out the aforementioned wireless communication with the control apparatus 10.

The measurement unit 43 includes a photodetector 43A such as a light-receiving element. A measurement area such as a fingertip, an earlobe, or the like is irradiated with red light and infrared light from a light-emitting element (not shown), and the photodetector 43A receives light that has passed through the measurement area or has been reflected by the measurement area. Hemoglobin in the blood absorbs red light and infrared light at different rates depending on how oxygenated the hemoglobin is, and the measurement unit 43 measures the blood oxygenation level based on an amount of light received by the photodetector 43A.

Figure 5:
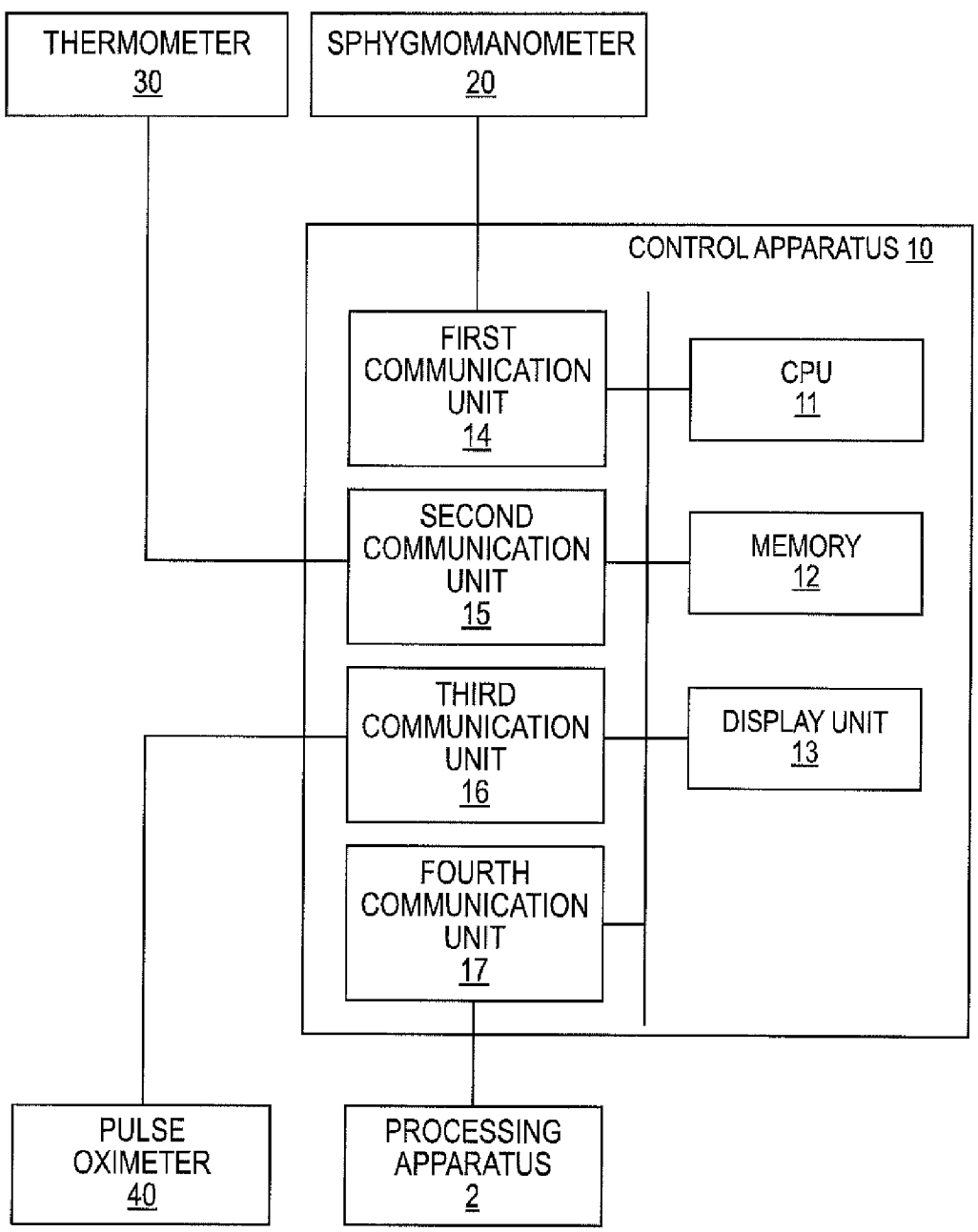
FIG. 5 is a block diagram illustrating a specific example of the device configuration of a control apparatus belonging to the biological information monitor.

FIG. 5 is a block diagram illustrating a specific example of the device configuration of the control apparatus 10.

The control apparatus 10 has, as described above, essentially the same configuration as a typical personal computer. Specifically, as shown in FIG. 5, the control apparatus 10 includes: a CPU 11 for controlling the control apparatus 10 as a whole; a memory 12 for storing programs executed by the CPU 11, information for use in computations performed by the CPU 11, received measurement values, and so on; the display unit 13; a first communication unit 14 for carrying out the aforementioned wireless communication with the blood pressure meter 20; a second communication unit 15 for carrying out the aforementioned wireless communication with the thermometer 30; a third communication unit 16 for carrying out the aforementioned wireless communication with the pulse oximeter 40; and a fourth communication unit 17 for communicating with the processing apparatus 2.

Outline of Operations

It is assumed that the biological information monitor 1 is originally associated with the measurement subject. In other words, the blood pressure meter 20, the thermometer 30, and the pulse oximeter 40 belonging to the biological information monitor 1 are associated with the same measurement subject, and furthermore, those measurement devices are associated with the control apparatus 10.

As described above, it is not necessary to connect the respective measurement devices to the control apparatus 10 using a communication line because the respective measurement devices communicate with the control apparatus 10 wirelessly. In other words, the connection between the respective measurement devices and the control apparatus 10 is cableless. Accordingly, there may be cases where measurement values from measurement devices belonging to another biological information monitor that is unrelated to the control apparatus 10 are transmitted to the control apparatus 10, such as when the other biological information monitor is present in the immediate vicinity.

Here, there are also cases where, as described above, the measurement values from those measurement devices are not measurement values that have been measured from the measurement subject associated with the biological information monitor 1, and if the measurement values from the respective measurement devices, including the unassociated measurement values, are then associated as a measurement value group, a problem in which the data becomes mixed up will occur.

In addition, there may be cases where the measurement subject associated with the biological information monitor 1 mistakenly takes a measurement using a measurement device belonging to the other biological information monitor and transmits that measurement value to the control apparatus 10 of the biological information monitor 1 associated with that measurement subject him/herself.

This is problematic in terms of sanitation, because measurement devices often take measurements by coming into direct contact with a measurement area.

Therefore, according to the biological information monitor 1 of the present embodiment, when associating the measurement values transmitted from the respective measurement devices, the control apparatus 10 associates the values after first authenticating the stated measurement devices as belonging to the biological information monitor 1.

Figure 6:
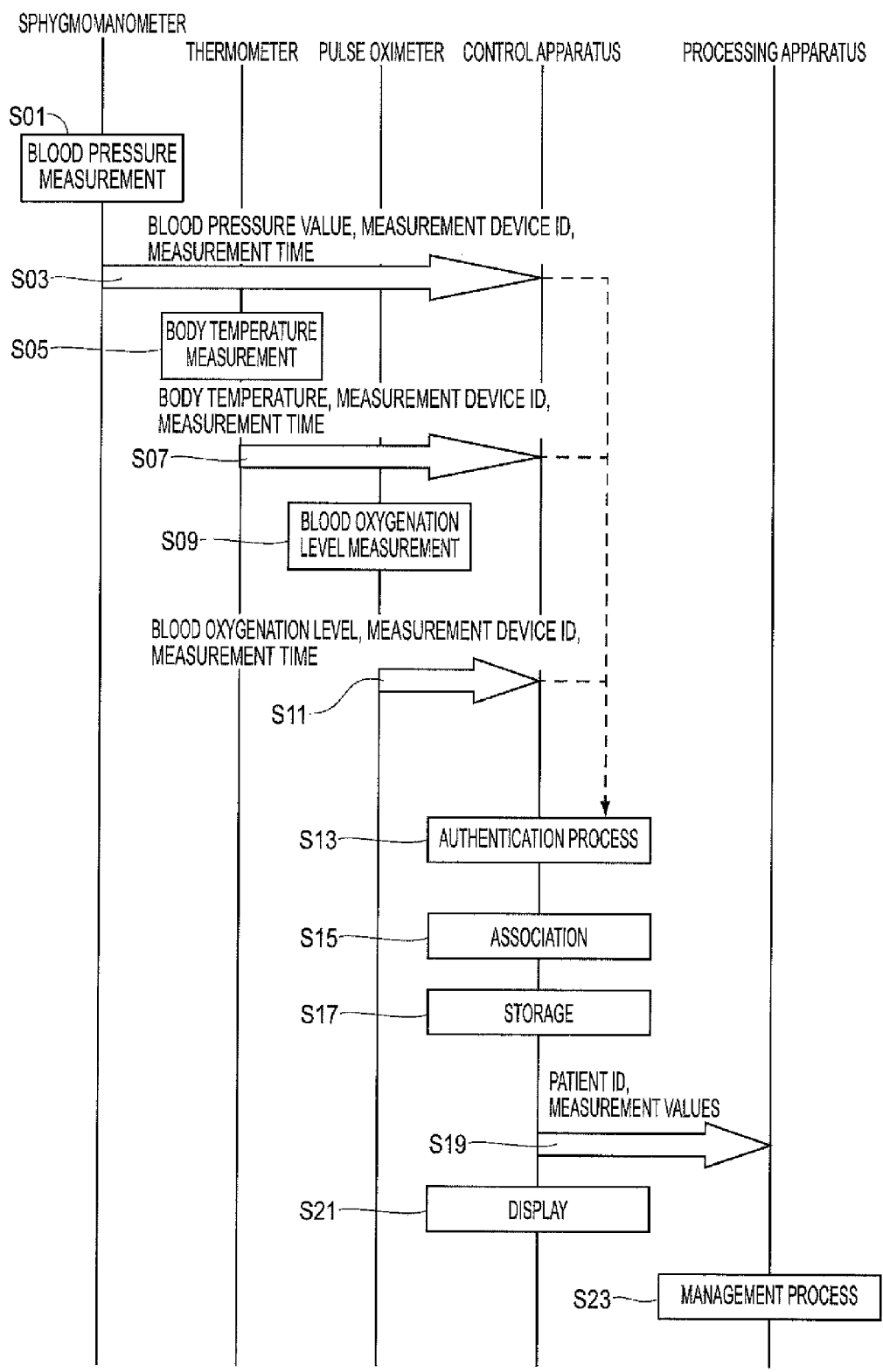
FIG. 6 is a diagram illustrating an overview of operations performed by the biological information monitor.

FIG. 6 is a diagram illustrating an overview of operations performed by the biological information monitor 1 according to the present embodiment.

As shown in FIG. 6, when the operations start, the blood pressure of the measurement subject associated with the biological information monitor 1 is measured using the blood pressure meter 20 in step S01. Then, in step S03, the blood pressure meter 20 transmits the measured blood pressure value and the stored measurement device ID that serves as identification information of the blood pressure meter 20 to the control apparatus 10 along with information identifying a measurement time.

In step S05, the body temperature of the measurement subject associated with the biological information monitor 1 is measured using the thermometer 30. Then, in step S07, the thermometer 30 transmits the measured body temperature and the stored measurement device ID that serves as identification information of the thermometer 30 to the control apparatus 10 along with information identifying a measurement time.

In step S09, the blood oxygenation level of the measurement subject associated with the biological information monitor 1 is measured using the pulse oximeter 40. In step S11, the pulse oximeter 40 transmits the measured blood oxygenation level and the stored measurement device ID that serves as identification information of the pulse oximeter 40 to the control apparatus 10 along with information identifying a measurement time.

Note that the order of the measurements taken using these measurement devices is not limited to the order illustrated in FIG. 6.

In step S13, the control apparatus 10 uses the information transmitted from the respective measurement devices to perform an authentication process for authenticating the received measurement values as having been transmitted from measurement devices that belong to the biological information monitor 1. In other words, the control apparatus 10 stores the measurement values transmitted from the respective measurement devices as described above along with an indication that the measurement times thereof fall within a predetermined amount of time. Then, the respective measurement devices are authenticated as being measurement devices belonging to the biological information monitor 1 by confirming whether or not the respective measurement device IDs transmitted with measurement values of the respective measurement devices that are already stored are the same as the measurement device IDs transmitted along with the measurement values in the aforementioned steps S03, S07, and S11.

The reason for this is that as described above, the biological information monitor 1 is associated with the measurement subject, and measurement values that were previously transmitted can be considered measurement values taken by the measurement subject using the respective measurement devices belonging to the biological information monitor 1; accordingly, in the case where the measurement device IDs transmitted along with the measurement values this time are the same as the measurement device IDs of the respective measurement devices that were transmitted along with previous measurement values, it is assumed that those measurement values are values from the respective measurement devices belonging to the biological information monitor 1.

In the case where the authentication in step S13 has succeeded, or in other words, in the case where the measurement device IDs transmitted along with the measurement values in the aforementioned steps S03, S07, and S11 are the same as the measurement device IDs transmitted previously along with the measurement values that are already stored, in step S15, the control apparatus 10 associates the measurement values transmitted from the respective measurement devices with each other. Here, it is preferable for the association to occur in the case where the measurement times of the respective measurement values fall within a predetermined amount of time set in advance. Then, in step S17, the group of associated measurement values are stored in a predetermined region of the memory 12. In step S19, the values are transmitted to the processing apparatus 2. Preferably, a correspondence relationship between at least one of the measurement device IDs and information for identifying the measurement subject (also called a "patient ID" hereinafter) is stored in the control apparatus 10, and in step S19, the group of associated measurement values is transmitted to the processing apparatus 2 along with the corresponding patient ID.

In step S21, the group of associated measurement values is displayed in the display unit 13.

In the processing apparatus 2, a management process is executed on the received measurement values by executing the installed management application 2A (step S23). This corresponds to, for example, a process for writing the measurement values into an electronic medical record of the measurement subject corresponding to the associated patient ID.

Functional Configuration

The functional configurations of the blood pressure meter 20, the thermometer 30, and the pulse oximeter 40 serving as the measurement devices generally have identical functional configurations for performing standard measurement. In other words, the blood pressure meter 20, the thermometer 30, and the pulse oximeter 40 serving as the measurement devices each have functions for performing operations such as those described hereinafter.

Upon accepting the input of an operation signal instructing measurement to start from an operation switch or the like (not shown), the CPU reads out a program stored in the memory and performs a measurement operation using the measurement unit. The CPU includes a timer function (not shown). The CPU transmits the measurement value obtained through this operation, and the measurement device ID serving as information stored in the memory for identifying that measurement device itself, along with information for identifying the measurement time to the control apparatus 10 at a predetermined timing.

Figure 7:
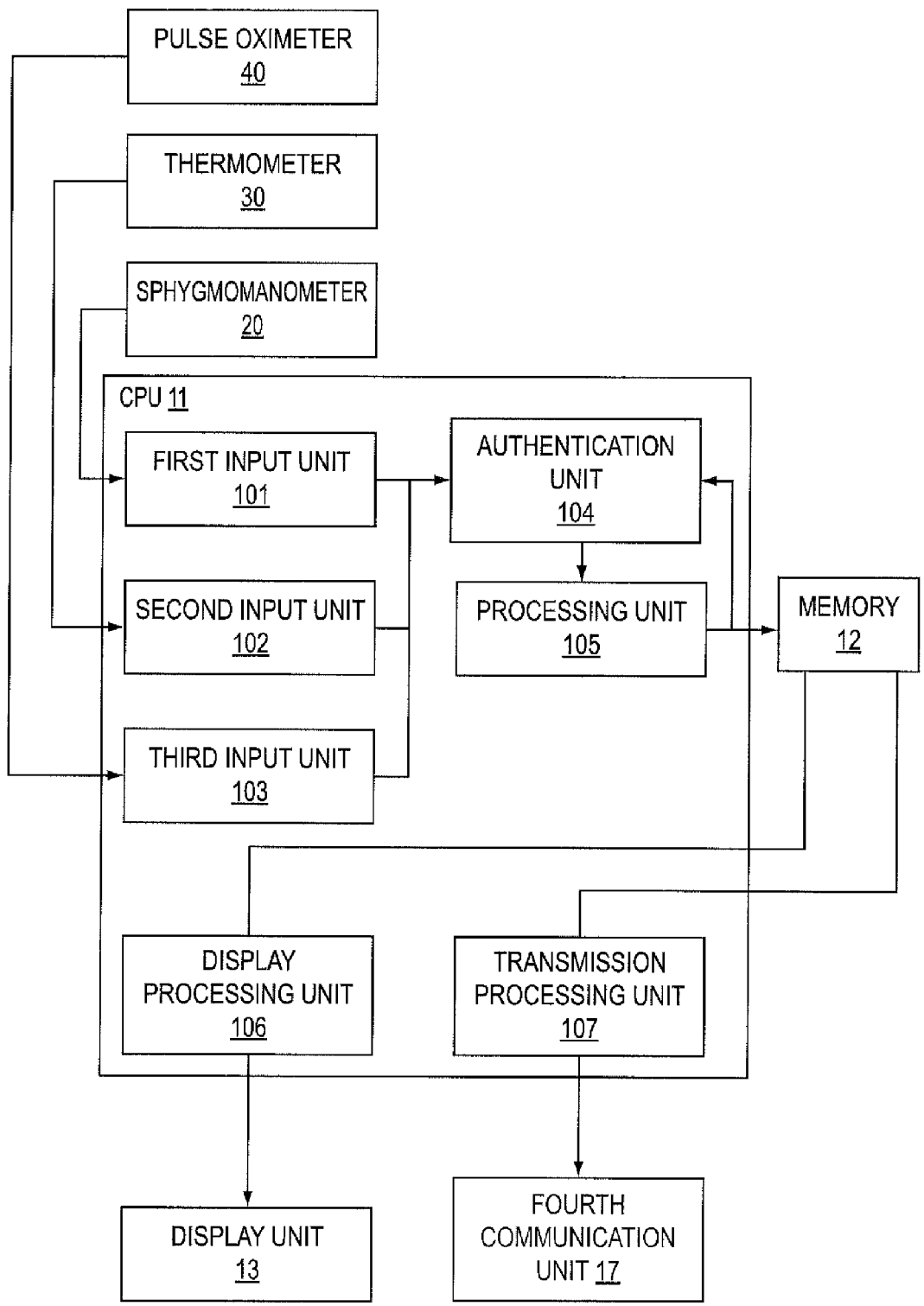
FIG. 7 is a block diagram illustrating a specific example of the functional configuration of the control apparatus.

FIG. 7 is a block diagram illustrating a specific example of the functional configuration of the control apparatus 10. The respective functions shown in FIG. 7 are primarily implemented in the CPU 11 of the control apparatus 10 by the CPU 11 reading out and executing programs stored in the memory 12. However, at least some of these functions may be implemented using a hardware configuration such as electric circuits or the like.

As shown in FIG. 7, the control apparatus 10 includes: a first input unit 101 for accepting the input of information transmitted from the blood pressure meter 20 via the first communication unit 14; a second input unit 102 for accepting the input of information transmitted from the thermometer 30 via the second communication unit 15; a third input unit 103 for accepting the input of information transmitted from the pulse oximeter 40 via the third communication unit 16; an authentication unit 104 for performing authentication by comparing the measurement device IDs inputted along with measurement values from the respective measurement devices and already stored in a predetermined region of the memory 12 with the measurement device IDs newly inputted along with the measurement values from the respective measurement devices; a processing unit 105 for storing, in a predetermined region of the memory 12, measurement values that have been associated through a process for associating the measurement values inputted from the respective measurement devices based on an authentication result; a display processing unit 106 for executing a process for displaying the associated measurement values stored in the memory 12 in the display unit 13; and a transmission processing unit 107 for executing a process for transmitting the associated measurement values in correspondence with the patient ID to the processing apparatus 2 via the fourth communication unit 17.

Figure 8:
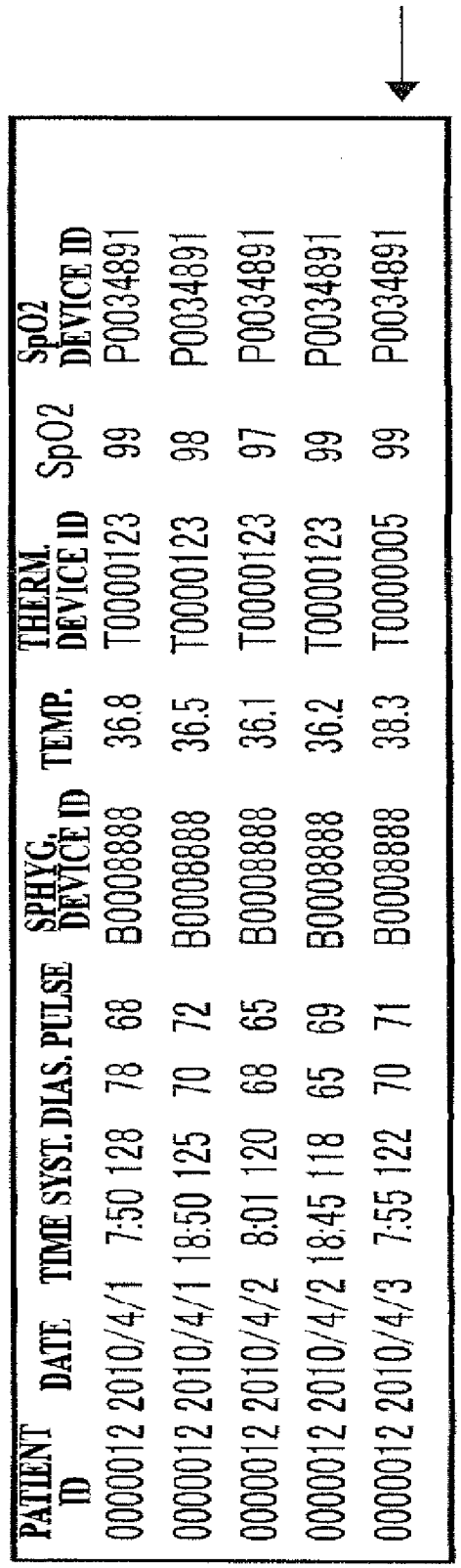
FIG. 8 is a diagram illustrating a specific example of measurement values stored in a predetermined region of a memory in the control apparatus.

FIG. 8 is a diagram illustrating a specific example of measurement values stored in the predetermined region of the memory 12.

As shown in FIG. 8, when the aforementioned authentication succeeds, the processing unit 105 stores the measurement values inputted from the respective measurement devices in association with the measurement device IDs of the respective measurement devices. For example, as shown in FIG. 8, measurement values for which the measurement time is within an amount of time specified in advance are handled as measurement values measured at essentially the same timing; the measurement time of one of those measurement values is taken as a representative measurement time, and a measurement value group is stored for each of those measurement times. In the example shown in FIG. 8, each line indicates a measurement value group associated with a single measurement time.

Upon accepting the input of a blood pressure value serving as the measurement value from the blood pressure meter 20 and the measurement device ID that identifies the blood pressure meter 20, the authentication unit 104 compares the inputted measurement device ID with a measurement device ID already stored along with a blood pressure value in a predetermined region of the memory 12 and determines whether or not the two IDs match. Likewise, for the measurement device IDs identifying the thermometer 30 and the pulse oximeter 40 that have been inputted along with the measurement values from those measurement devices, the authentication unit 104 compares the inputted measurement device IDs with measurement device IDs already stored along with a body temperature or a blood oxygenation level in a predetermined region of the memory 12, and determines whether or not the respective IDs match.

The authentication unit 104 compares each measurement device ID with measurement device IDs that have been inputted previously and are already stored in the memory 12. This comparison may be a comparison with only the most recently inputted measurement ID, a comparison with a predetermined number of measurement device IDs spanning back from the most recent measurement device ID, a comparison with the oldest stored measurement device ID, or a comparison with all of the stored measurement device IDs. Preferably, the inputted measurement device ID is compared to the most recent measurement device ID and the measurement device ID previous thereto. Doing so makes it possible to prevent frequent warnings in the case where the measurement subject uses different measurement devices for each measurement.

Note that no measurement device IDs are stored in the memory 12 in its initial state, and thus a case is conceivable in which when the second input is made, the authentication is carried out using the first measurement device ID inputted into the memory 12. Doing so makes it possible to ensure that the same measurement device as the measurement device used the first time, is used the second and subsequent times.

On the other hand, as another method, a subsequent authentication may be made using the measurement device ID inputted the first time as a provisional ID, and in the case where that subsequent authentication has succeeded, or in other words, in the case where the same measurement device ID has been inputted the first time and the second time, that measurement device ID may be used in the authentications that occur thereafter. Through this, the subsequent authentications can be carried out having finalized the measurement devices that belong to the biological information monitor 1.

As will be described later, in the case where the authentication has failed, the measurement device IDs of the measurement devices for which the authentication has failed may be stored as provisional IDs and those measurement device IDs (provisional IDs) may then be used by the authentication unit 104 the next time. Here, in the case where the authentication has succeeded using a provisional ID, the provisional ID may be stored as the measurement device ID of the measurement device belonging to the biological information monitor 1 and used in the authentications that follow thereafter. Accordingly, even if the measurement devices in the biological information monitor 1 are changed partway through, the authentication will not fail each time such a change is made, thus maintaining a level of convenience for the user.

The authentication unit 104 performs authentication for each measurement device and determines whether the authentication has succeeded or failed. Then, in the case where the authentication performed by the authentication unit 104 has succeeded, the processing unit 105 associates the measurement values and stores the respective measurement device IDs along with information for identifying the measurement time when the group of measurement values was obtained in a predetermined region of the memory 12.

At this time, it is preferable to accept the input of the patient ID along with the measurement value from at least one of the measurement devices, and for the processing unit 105 to store the associated group of measurement values along with the patient ID in the case where the authentication performed by the authentication unit 104 has succeeded.

As another example, the input of the patient ID may be accepted from an input means (not shown) of the control apparatus 10 when the measurement values are inputted, and the group of measurement values may be stored along with the patient ID. This input means may be, for example, a means through which the patient ID is inputted directly, such as a keyboard, or may be a means that is connected to a reading device for reading a patient ID stored in an IC tag or the like and that accepts the input of that information.

In addition, the processing unit 105 may associate and store the measurement values inputted from all of the measurement devices only in the case where the authentication performed by the authentication unit 104 has succeeded for all of the measurement devices, or may associate only the measurement values from measurement devices for which the authentication has succeeded and store those measurement values in a predetermined region of the memory 12. With the former, all of the types of measurement values specified in advance for a single measurement, namely the blood pressure value, body temperature, and blood oxygenation level, are stored together in association with the measurement time. Meanwhile, with the latter, in the case where a measurement has been taken using at least one of the measurement devices belonging to the biological information monitor 1 during a single measurement, the measurement value obtained using that measurement device is stored.

Furthermore, the processing unit 105 may store information in the memory 12 even in the case where the authentication performed by the authentication unit 104 has failed. In the example shown in FIG. 8, the measurement device ID of the thermometer 30 (a thermometer device ID) in the measurement value group on the fifth line is different from the previous measurement device ID of the thermometer 30. In the case where the display processing unit 106 displays this measurement value group, it is preferable for the body temperature to be displayed along with an indication that the body temperature was measured using a different thermometer than the thermometer 30 belonging to the biological information monitor 1. Meanwhile, when transmitting the series of measurement values associated with that measurement time to the processing apparatus 2 at a predetermined timing, the transmission processing unit 107 may refrain from transmitting only the body temperature, or may add information indicating that the body temperature was measured using a different thermometer than the thermometer 30 belonging to the biological information monitor 1 and transmit the body temperature along with that information.

The following descriptions assume that measurement values from measurement devices for which the authentication has failed are used only for display purposes, and that only measurement values from measurement devices for which authentication has succeeded are associated with measurement device IDs, stored along with the respective measurement times, and transmitted to the processing apparatus 2 at a predetermined timing.

Flow of Operations

Figure 9:
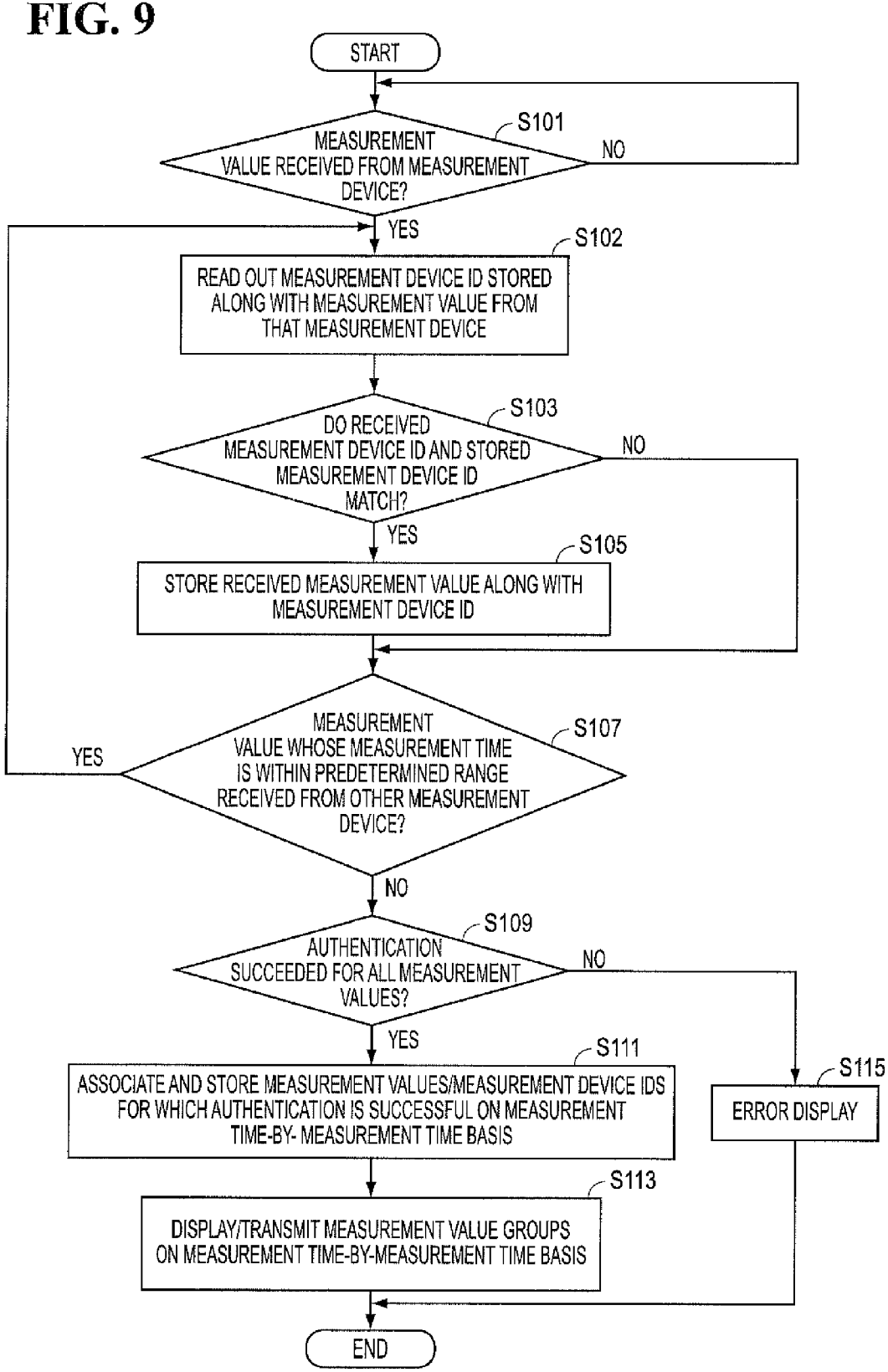
FIG. 9 is a flowchart illustrating operations performed by the control apparatus.
Figure 12:
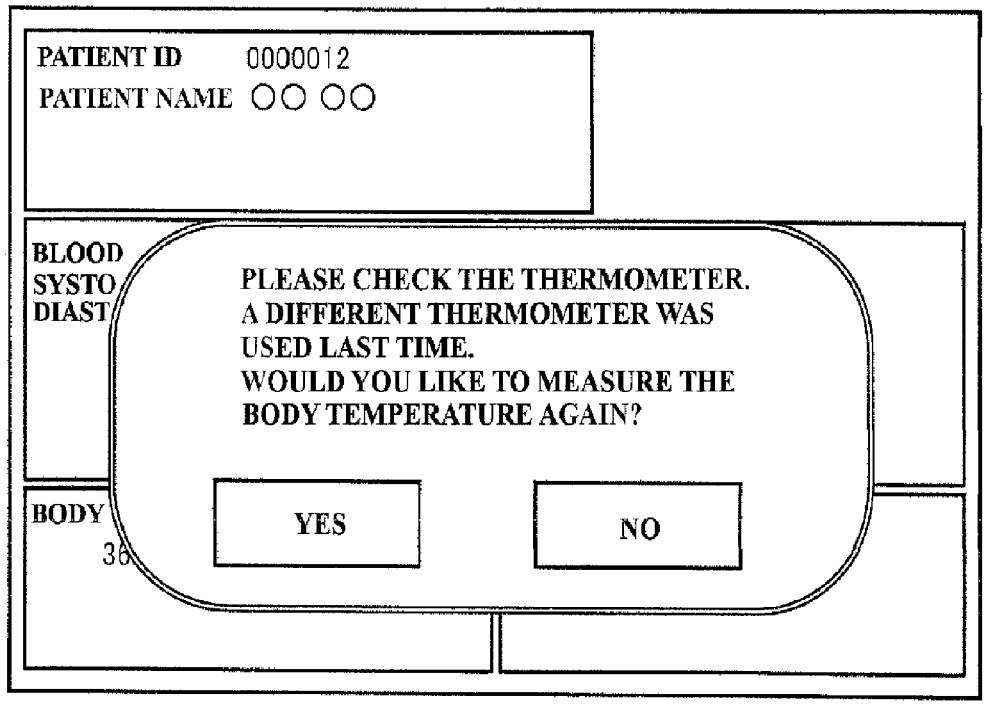
FIG. 12 is a diagram illustrating an example of a screen generated by the control apparatus.

FIG. 9 is a flowchart illustrating operations performed by the control apparatus 10. The operations illustrated in the flowchart in FIG. 9 are realized by the CPU 11 of the control apparatus 10 reading out and executing programs stored in the memory 12 in order to implement the respective functions illustrated in FIG. 7. In addition, FIGS. 10 to 12 are diagrams illustrating examples of screens displayed in the display unit 13 as a result of operations performed by the control apparatus 10.

As shown in FIG. 9, the CPU 11 stands by for the input of a measurement value from a measurement device.

At this time, the CPU 11 may display a screen indicating that no measurement values have been inputted from any of the measurement devices ("no measurement"), as shown in FIG. 10. Preferably, in the case where the control apparatus 10 already stores an associated patient ID, that patient ID may be displayed as shown in FIG. 10.

When it has been detected that a measurement value has been received from a measurement device (YES in step S101), in step S102, the CPU 11 reads out, from the measurement values stored in a predetermined region of the memory 12, the measurement device ID that is stored along with the same type of measurement value as the received measurement value. Then, the CPU 11 compares the measurement device ID received along with the measurement value in step S101 with the measurement device ID read out in step S102 and determines whether or not those IDs match, and authenticates that measurement device as being the same as a measurement device used in a past measurement, or in other words, authenticates the measurement device as being a measurement device belonging to the biological information monitor 1.

Here, it is preferable to read out the measurement device IDs, stored in a predetermined region of the memory 12, that are respectively associated with the same type of measurement value as the measurement value received immediately before step S101 and with the same type of measurement value as the measurement value immediately previous to that measurement value, and for the measurement device ID received along with the measurement value in step S101 to be compared thereto.

In the case where the authentication result indicates that the measurement IDs match (YES in step S103), the CPU 11 authenticates the measurement device used to obtain the measurement value received in step S101 as matching a measurement device used previously, or in other words, authenticates the measurement device used this time as being a measurement device that belongs to the biological information monitor 1, and stores the measurement value received in step S105 along with the measurement device ID.

On the other hand, in the case where the authentication has failed, or in other words, in the case where the read-out measurement device ID and the received measurement device ID do not match (NO in step S103), the CPU 11 determines that the measurement device used to obtain the measurement value received in step S101 does not match a measurement device used previously, or in other words, that the measurement device used for this measurement is not a measurement device that belongs to the biological information monitor 1, and skips the process of step S105.

The CPU 11 repeats the processes of steps S102 to S105 each time a measurement value is received from another measurement device at a measurement time within a range specified in advance, and performs the authentication as to whether the measurement values have been measured using a measurement device belonging to the biological information monitor 1. When the authentication succeeds, the measurement value is stored along with the respective measurement device ID in step S105.

When measurement values have been successfully received from each of the blood pressure meter 20, the thermometer 30, and the pulse oximeter 40 at measurement times that are within the stated pre-specified range (NO in step S107), and all of these measurement devices have been authenticated as matching measurement devices used in previous measurements (YES in step S109), in step S111, the CPU 11 associates the received measurement values with the measurement device IDs and stores the measurement values and measurement device IDs in a predetermined region of the memory 12 on a measurement time-by-measurement time basis. In step S113, the CPU 11 displays the associated measurement value group, and transmits the measurement value group to the processing apparatus 2 at a predetermined timing.

FIG. 11 illustrates a specific example of a screen displayed in the case where the measurement device IDs transmitted along with the measurement values from the blood pressure meter 20, the thermometer 30, and the pulse oximeter 40 have all been successfully authenticated; as shown in FIG. 11, in this case, the measurement values are displayed as a group of associated measurement values measured at an associated timing (that is, within a certain amount of time). Furthermore, in the case where the control apparatus 10 has accepted the input of a patient ID along with the measurement values, or in the case where a patient ID associated with the biological information monitor 1 is already stored, the patient ID (000012) is displayed in a single screen in association with the measurement values.

On the other hand, in the case where even one of the measurement devices from which the measurement values were received is different from the measurement devices used in previous measurements and the authentication thereof has thus failed (NO in step S109), in step S115, the CPU 11 displays an indication that the authentication has failed (that is, displays an error display). FIG. 12 illustrates a specific example of a screen displayed in the case where the authentication has failed, or in other words, in the case where even one of the measurement device IDs inputted along with the blood pressure, the body temperature, and the blood oxygenation level is different from the stored measurement device IDs used in previous measurements.

The example shown in FIG. 12 is an example of a screen based on the example shown in FIG. 8, in which the device ID inputted along with the body temperature does not match the measurement device ID stored in the memory 12 along with the previous body temperature. In this case, as shown in FIG. 12, a message indicating that the thermometer is different from the thermometer used in the previous measurement is displayed.

At this time, it is preferable for the CPU 11 to display the message while displaying the measurement values transmitted from the respective measurement devices. The body temperature for which the authentication failed may be included in these measurement values.

Furthermore, as shown in FIG. 12, the CPU 11 may provide a means for instructing a measurement to be carried out again in the aforementioned step S15.

That is, in this example, it has been determined that the thermometer used for this measurement is different from the thermometer 30 belonging to the biological information monitor 1, and thus in step S15, the CPU 11 displays a means (a button, in the example shown in FIG. 12) for inputting an instruction as to whether to associate and store that measurement value with another measurement value or to measure the body temperature again. This display may be performed along with the error display in step S15 as shown in FIG. 12, or may be performed after the error display. When an instruction to perform the measurement again has been accepted using the stated means, the CPU 11 returns the process to the beginning and once again stands by for the input of a measurement value.

Note that a case in which one of the measurement devices that transmitted a measurement value to the control apparatus 10 is a measurement device belonging to another biological information monitor can be given as an example of a case in which the authentication fails. Here, in the case where the biological information monitors and the measurement subjects correspond one-to-one and the control apparatus 10 stores correspondence relationships between other biological information monitors and measurement subjects (patient IDs), preferably, the CPU 11 may identify the patient IDs corresponding to the measurement device IDs inputted along with the measurement values and display that information.

Figure 13:
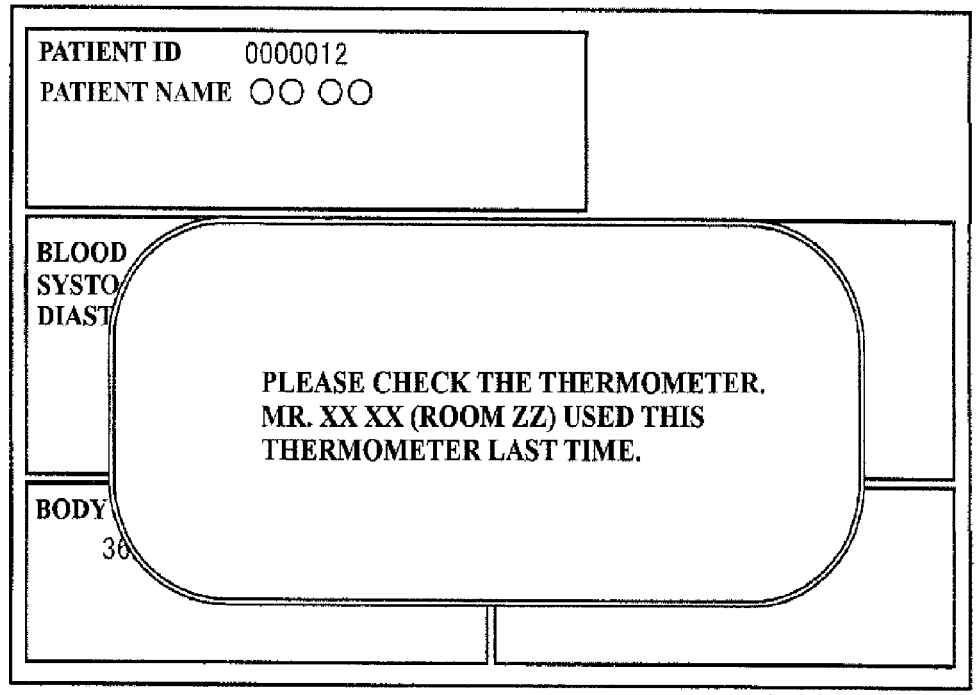
FIG. 13 is a diagram illustrating an example of a screen generated by the control apparatus.

FIG. 13 is another specific example of a display screen, and is an example of a screen based on the example shown in FIG. 8. That is, it is determined, in the example shown in FIG. 8, that the measurement device ID of the thermometer is different from the previous measurement device ID.

Here, in the case where correspondence relationships between the respective measurement device IDs and measurement subjects (patient IDs) are stored in advance in the control apparatus 10, the patient ID associated with the different measurement device ID is identified. Then, as shown in FIG. 13, information based on the identified patient ID (in the example shown in FIG. 13, the name and room number of the measurement subject) may be displayed.

Effects of the Embodiment

By operating in this manner, in the case where measurements of biological information are taken by a plurality of measurement devices belonging to the biological information monitor 1 that are used independently from the control apparatus 10 and the results of the measurements are then transmitted to the control apparatus 10, the biological information monitor 1 according to the embodiment determines whether or not the respective measurement devices are measurement devices that have been used previously.

The measurement devices are authenticated as belonging to the biological information monitor 1 by performing this determination. In the case where the biological information monitor 1 is originally associated with a measurement subject, that measurement subject can be associated with the measurement values taken using the respective measurement devices.

Through this, whether the measurement devices that transmitted the measurement values match with the measurement devices belonging to the biological information monitor 1 can be authenticated through a simple process and without requiring an operation for registering IDs of the respective measurement devices in the control apparatus 10 in advance, and the measurement subject associated with the biological information monitor 1 can then be associated with the measurement values from the respective measurement devices.

Through this, the mistaken use of measurement devices belonging to another biological information monitor can be prevented, and an effect of improving sanitation can also be achieved.

In addition, the measurement values of a measurement subject associated with another biological information monitor can be prevented from being mistakenly transmitted to the biological information monitor 1, which makes it possible to prevent patients from becoming mixed up with each other.

Variations

The above descriptions illustrate a case in which the control apparatus 10 belongs to the biological information monitor 1. However, the control apparatus 10 may be incorporated into one of the measurement devices. In other words, one of the measurement devices may function as the control apparatus 10. For example, a case in which the blood pressure meter 20 functions as the control apparatus 10 can be considered.

In this case, the blood pressure meter 20 stores a measurement value (a blood pressure value) it measured itself, and also accepts the input of a body temperature and measurement device ID from the thermometer 30 along with a blood oxygenation level and measurement device ID from the pulse oximeter 40; then, by comparing stored measurement device IDs that were inputted previously with the measurement device IDs inputted this time, the blood pressure meter 20 authenticates that the inputted measurement values are measurement values from the thermometer 30 and the pulse oximeter 40 belonging to the biological information monitor 1 to which the blood pressure meter 20 itself belongs.

At this time, using human body communication for the communication between the blood pressure meter 20 and the thermometer 30 and for the communication between the blood pressure meter 20 and the pulse oximeter 40 ensures that the measurement values are transmitted to the blood pressure meter 20 while the respective measurement devices are affixed to the measurement subject for measurement, which makes it possible to confirm the values simultaneously.

Furthermore, a program for causing the control apparatus 10 configured of a generic personal computer to execute the aforementioned processes can also be provided. Such a program can be recorded on a computer-readable recording medium such as a flexible disk, a CD-ROM (compact disc read-only memory), a ROM (read-only memory), a RAM (random access memory), or a memory card that is supplied to a computer, and can be provided in such form as a program product. Alternatively, the program can be recorded on a recording medium such as a hard disk mounted within a computer, and can be provided in such form as a program. Further still, the program can also be downloaded via a network, and can be provided in such form as a program.

Note that the program according to the present invention may execute processing by calling, in a predetermined arrangement and at a predetermined timing, the necessary program modules from among the modules provided as part of an operating system (OS) of a computer. In this case, the stated modules are not included in the program itself, and the processing is executed in cooperation with the OS. Such a program that does not include modules in this manner can also fall within the scope of the program according to the present invention.

In addition, the program according to the present invention may be provided having been incorporated into a part of another program. In such a case as well, modules included in the stated other program are not included within the program itself, and the processing is executed in cooperation with the other program. Such a program that is incorporated into another program can also fall within the scope of the program according to the present invention.

The program product that is provided is installed in a program storage unit such as a hard disk and executed. Note that the program product includes the program itself and the recording medium on which the program is recorded.

While the invention has been described in detail, the foregoing descriptions are to be considered as examples only and not as limiting in any way; it is also to be understood that the scope of the invention is to be interpreted based on the scope of the appended claims.

REFERENCE SIGNS LIST

1 biological information monitor
2 processing apparatus
2A management application
10 control apparatus
11, 21, 31, 41 CPU
12, 22, 32, 42 memory
13 display unit
14 first communication unit
15 second communication unit
16 third communication unit
17 fourth communication unit
20 blood pressure meter
23, 43 measurement unit
23A pressure sensor
24, 34, 45 communication unit
30 thermometer
33 body temperature measurement unit
33A temperature sensor
40 pulse oximeter
43A photodetector
101 first input unit
102 second input unit
103 third input unit
104 authentication unit
105 processing unit
106 display processing unit
107 transmission processing unit

The invention claimed is:

1. A wireless, self-authenticating biological information monitoring system comprising:
   a first health measurement-type device that is a blood pressure meter including a blood pressure sensor that is configured to measure a first health measurement-type value; and
   a second health measurement-type device that measures a different biological characteristic than the blood pressure meter, and is provided separately from the first health measurement-type device, the second health measurement-type device having a unique device identifier that is different from a unique device identifier of the first health measurement-type device, the second health measurement device being configured to:
   (i) measure a second health measurement-type value, (ii) generate a time of measurement of the second health measurement-type value, the time of measurement of the second health measurement-type value being a time when the second health measurement-type value was measured, and (iii) wirelessly transmit the measured second health measurement-type value, the unique device identifier of the second health measurement-type device and the time of measurement of the second health measurement-type value to the first health measurement-type device;

wherein the first health measurement-type device comprises:

a wireless communication interface that wirelessly communicates with at least the second health measurement-type device, a memory, and a processor programmed to:

store, in the memory, the unique device identifier of the first health measurement-type device in association with a unique patient identifier of a measurement subject;

receive, via the wireless communication interface from the second health measurement-type device, a first measurement of the second health measurement-type value, the unique device identifier of the second health measurement-type device, and a time of measurement of the first measurement of the second health measurement-type value;

store the received unique device identifier of the second health measurement-type device in the memory as a provisional device identifier;

receive a measurement of the first health measurement-type value and generate a time of measurement of the measurement of the first health measurement-type value, the time of measurement of the measurement of the first health measurement-type value being a time when the measurement of the first health measurement-type value was measured;

receive, via the wireless communication interface from the second health measurement-type device, a second measurement of the second health measurement-type value, the unique device identifier of the second health measurement-type device that transmitted the second measurement of the second health measurement-type value, and a time of measurement of the second measurement of the second health measurement-type value;

determine whether the second health measurement-type device that transmitted the second measurement of the second health measurement-type value has been previously-used by determining whether the unique device identifier of the second health measurement-type device that transmitted the second measurement of the second health measurement-type value matches the stored provisional device identifier;

successfully authenticate the second health measurement-type device that transmitted the second measurement of the second health measurement-type value as being the same as the previously-used second health measurement-type device when the result of the determination indicates that the unique device identifier of the second health measurement-type device that transmitted the second measurement of the second health measurement-type value matches the stored provisional device identifier; and when the second health measurement-type device that transmitted the second measurement of the second health measurement-type value has been successfully authenticated, and the time of measurement of the measurement of the first health measurement-type value and the time of measurement of the second measurement of the second health measurement-type value are both measurement times that fall within a predetermined amount of time, associate and store together both the measurement of the first health measurement-type value and the second measurement of the second health measurement-type value as a measurement value group in a predetermined region of the memory.

2. The biological information monitoring system according to claim 1, wherein the processor is further programmed to:

when the received unique device identifier of the second health measurement-type device that transmitted the second measurement of the second health measurement-type value does not match either the stored provisional device identifier, or a unique device identifier stored in the predetermined region of the memory: (i) determine that authentication has failed, and (ii) output failure information to a display of the first health measurement-type device, the output failure information indicating that the first health measurement-type device has failed to authenticate the second health measurement-type device.

3. The biological information monitoring system according to claim 1, wherein the processor is further programmed to: when the second health measurement-type device that transmitted the second measurement of the second health measurement-type value has been successfully authenticated, store the associated measurement of the first health measurement-type value and the second measurement of the second health measurement-type value along with the unique device identifier of the first health measurement-type device and the unique device identifier of the second health measurement-type device that transmitted the second measurement of the second health measurement-type value in the predetermined region of the memory on a measurement time-by-measurement time basis.

4. A wireless, self-authenticating biological information monitoring method comprising:

storing in a memory of a first health-measurement type device, by the first health measurement-type device, a unique device identifier of the first health measurement-type device in association with a unique patient identifier of a measurement subject, the first health measurement-type device being a blood pressure meter including blood pressure sensor that is configured to measure a first health measurement-type value;

receive, via a wireless communication interface of the first health measurement-type device, from a second health measurement-type device, a first measurement of a second health measurement-type value, a unique device identifier of the second health measurement-type device, and a time of measurement of the first measurement of the second health measurement-type value, which is a time when the first measurement of the second health measurement-type value was measured, the second health measurement-type value being a different biological characteristic than the first health measurement-type value measured by the blood pressure meter, the second health measurement-type device being provided separately from the first health measurement-type device, the unique device identifier of the second health measurement-type device being different from the unique device identifier of the first health measurement-type device;

storing, by the first health measurement-type device, the received unique device identifier of the second health measurement-type device, in a memory of the first health-measurement type device, as a provisional device identifier;

measuring, by the first health measurement-type device, a measurement of the first health measurement-type value;

generating, by the first health measurement-type device, a time of measurement of the measurement of the first health measurement-type value;

measuring, by the second health measurement-type device, a second measurement of the second health measurement-type value;

generating, by the second health measurement-type device, a time of measurement of the second measurement of the second health measurement-type value representing a time when the second measurement of the second health measurement-type value was measured;

wirelessly transmitting, by the second health measurement-type device to the first health measurement-type device via a wireless communication interface of the second health measurement-type device, the second measurement of the second health measurement-type value, the unique device identifier of the second health measurement-type device and the time of measurement of the second measurement of the second health measurement-type value;

receiving, by the first health measurement-type device via the wireless communication interface of the first health measurement-type device, the second measurement of the second health measurement-type value, the time of measurement of the second measurement of the second health measurement-type value, and the unique device identifier of the second health measurement-type device that transmitted the second measurement of the second health measurement-type value;

determining, by the first health measurement-type device, whether the second health measurement-type device that transmitted the second measurement of the second health measurement-type value has been previously-used by determining whether the unique device identifier of the second health measurement-type device that transmitted the second measurement of the second health measurement-type value matches the stored provisional device identifier;

successfully authenticating, by the first health measurement-type device, the second health measurement-type device as being the same as the previously-used second health measurement-type device when the result of the determination indicates that the unique device identifier of the second health measurement-type device that transmitted the second measurement of the second health measurement-type value matches the stored provisional device identifier; and when the second health measurement-type device has been successfully authenticated, and the time of measurement of the measurement of the first health measurement-type value and the time of measurement of the second measurement of the second health measurement-type value both fall within a predetermined amount of time, associating together and storing, by the first health measurement-type device, both the measurement of the first health measurement-type value and the second measurement of the second health measurement-type value as a measurement value group in a predetermined region of the memory.

5. A first health measurement-type device comprising:
a blood pressure meter including a blood pressure sensor;
a wireless communication interface that wirelessly communicates with at least a second health measurement-type device, the second health measurement-type device being configured to measure a different biological characteristic than the blood pressure meter, and being provided separately from the first health measurement-type device, the second health measurement-type device having a unique device identifier that is different from a unique device identifier of the first health measurement-type device, the second health measurement device being configured to: (i) measure a second health measurement-type value, (ii) generate a time of measurement of the second health measurement-type value, the time of measurement of the second health measurement-type value being a time when the second health measurement-type value was measured, and (iii) wirelessly transmit the measured second health measurement-type value, the unique device identifier of the second health measurement-type device and the time of measurement of the second health measurement-type value to the first health measurement-type device;

a memory; and
a processor programmed to:
store, in the memory, the unique device identifier of the first health measurement-type device in association with a unique patient identifier of a measurement subject;

receive, via the wireless communication interface from the second health measurement-type device, a first measurement of the second health measurement-type value, the unique device identifier of the second health measurement-type device, and a time of measurement of the first measurement of the second health measurement-type value;

store the received unique device identifier of the second health measurement-type device in the memory as a provisional device identifier;

upon measurement by the blood pressure meter, receive a measurement of the first health measurement-type value and generate a time of measurement of the measurement of the first health measurement-type value, the time of measurement of the measurement of the first health measurement-type value being a time when the measurement of the first health measurement-type value was measured;

receive, via the wireless communication interface from the second health measurement-type device, a second measurement of the second health measurement-type value, the unique device identifier of the second health measurement-type device that transmitted the second measurement of the second health measurement-type value, and a time of measurement of the second measurement of the second health measurement-type value;

determine whether the second health measurement-type device that transmitted the second measurement of the second health measurement-type value has been previously-used by determining whether the received unique device identifier of the second health measurement-type device that transmitted the second measurement of the second health measurement-type value matches the stored provisional device identifier;

successfully authenticate the second health measurement-type device that transmitted the second measurement of the second health measurement-type value as being the same as the previously-used second health measurement-type device when the result of the determination indicates that the unique device identifier of the second health measurement-type device that transmitted the second measurement of the second health measurement-type value matches the stored provisional device identifier; and when the second health measurement-type device that transmitted the second measurement of the second health measurement-type value has been successfully authenticated, and the time of measurement of the measurement of the first health measurement-type value and the time of measurement of the second measurement of the second health measurement-type value are both measurement times that fall within a predetermined amount of time, associate and store together both the measurement of the first health measurement-type value and the second measurement of the second health measurement-type value as a measurement value group in a predetermined region of the memory.

6. The biological information monitoring system according to claim 1, wherein the processor of the first health measurement-type device is further programmed to:

when the received unique device identifier of the second health measurement-type device that transmitted the second measurement of the second health measurement-type value does not match either the stored provisional device identifier, or a unique device identifier stored in the predetermined region of the memory: (i) determine that authentication has failed, and (ii) control a display to display a button for inputting an instruction to store the second measurement of the second health measurement-type value in association with the first health measurement-type value in the predetermined region of the memory, and when the instruction to store has been input via the button, store the second measurement of the second health measurement-type value in association with the first health measurement-type value as the measurement value group in the predetermined region of the memory.

* * * * *